(12) United States Patent
Bartiss et al.

(10) Patent No.: US 11,951,084 B1
(45) Date of Patent: Apr. 9, 2024

(54) COMPOSITION FOR THE TREATMENT OF REFRACTORY PAINFUL INTERVERTEBRAL DISC RELATED DISORDERS AND METHOD FOR DELIVERY THEREOF TO TREAT THERETO

(71) Applicant: Progressive Health Partners, Zephyr Cove, NV (US)

(72) Inventors: Mark James Bartiss, Whiting, NJ (US); Daniel Bies, South Seaside Park, NJ (US); Dianne Dalton, Zephyr Cove, NV (US)

(73) Assignee: Progressive Health Partners, Zephyr Cove, NV (US)

( * ) Notice: Subject to any disclaimer, the term of this patent is extended or adjusted under 35 U.S.C. 154(b) by 0 days.

(21) Appl. No.: 18/141,112

(22) Filed: Apr. 28, 2023

(51) Int. Cl.
*A61K 31/165* (2006.01)
*A61K 33/06* (2006.01)

(52) U.S. Cl.
CPC .......... *A61K 31/165* (2013.01); *A61K 33/06* (2013.01)

(58) Field of Classification Search
CPC ....... A61K 33/06; A61K 33/14; A61K 31/195
See application file for complete search history.

(56) References Cited

U.S. PATENT DOCUMENTS 5,330,431 A * 7/1994 Herskowitz ........... A61M 5/148
604/153

FOREIGN PATENT DOCUMENTS

CN 107714718 A * 2/2018 ............. A61K 33/06
WO WO-2021184128 A1 * 9/2021

OTHER PUBLICATIONS

Dasgeb et al.(British Journal of Dermatology, Feb. 2018, vol. 178, pp. 350-356 (pp. 1-15)) (Year: 2018).*
Blatchley, (26th & 27th Annual Reports of the State Geologist of Indiana, Mineral Waters of Indiana, 1903, vol. 26, pp. 11-158) (Year: 1903).*
Colorado State University, (Colorado State University, Extension, Revised Dec. 2014) (Year: 2014).*
Poutaraud et al (Environmental and Experimental Botany, 2005, vol. 54, pp. 101-108) (Year: 2005).*
Blatchley, (26th & 27th Annual Reports of the State Geologist of Indiana, Mineral Waters of Indiana, 1903, vol. 26, pp. 11-158) Page to provide date for Blatchley reference, downloaded 2023 (Year: 2023).*
Kos (Med Arch., Dec. 2019, vol. 73, pp. 421-424) (Year: 2019).*
Healthline (Healthline.com, https://www.healthline.com/health/intravenous-medication-administration-what-to-know, Updated on Jul. 5, 2021) (Year: 2021).*
CN-107714718-A (Google English translation, downloaded 2023) (Year: 2023).*

* cited by examiner

*Primary Examiner* — Mark V Stevens
(74) *Attorney, Agent, or Firm* — Law Office of Vincent LoTempio, PLLC; Vincent G. LoTempio; Robert L. Cerasa

(57) ABSTRACT

The present application discloses a composition for the treatment of Painful Damaged Disc Syndrome (PDDS), disc bulge, protrusion and herniation, and a delivery method and recommended treatment protocol for delivering thereto to a subject with an effective dosage of the composition. The composition has anti-inflammatory, antioxidant and vasodilating and antispasmodic properties. The compound is being administered via intravenous drip over a specified period for pain relief.

1 Claim, 6 Drawing Sheets

| Age | Mean Estimated GFR (mL/min/1.73 m$^2$) |
|---|---|
| 20-29 | 116 |
| 30-39 | 107 |
| 40-49 | 99 |
| 50-59 | 93 |
| 60-69 | 85 |
| 70+ | 75 |

FIG. 3

COMPOSITION FOR THE TREATMENT OF REFRACTORY PAINFUL INTERVERTEBRAL DISC RELATED DISORDERS AND METHOD FOR DELIVERY THEREOF TO TREAT THERETO

FIELD OF INVENTION

The present application relates to the treatment of refractory intervertebral disc related syndromes and disorders, collectively referred to as Painful Damaged Disc Syndrome (PDDS), consisting of disc protrusion, bulge, and herniation. More particularly, the present application discloses a. pharmaceutical composition, method for delivery and recommended treatment protocol thereof to address pain related to PDDS whereas the subjects remaining treatment options are spinal epidural injections or spinal surgery.

BACKGROUND OF INVENTION

The human spine is comprised of 33 vertebra, and intervertebral discs exist between each spinal vertebra and serve to provide cushioning-they function as shock absorbers. (See FIG. 1)

An intervertebral disc is comprised of an outer layer called an annulus fibrous, which is a dense collagenous ring encircling the inner, jellylike portion of the disc called nucleus pulposus (see FIG. 1)

PDDS is used to describe the whole genre of disc pathology-including but not limited to disc bulge, prolapse, protrusion and herniation, giving rise to spinal pain and symptoms with or without radiculopathy. In the case of a disc bulge, prolapse and protrusion, the outer annulus area of the disc will bulge out. Disc herniation occurs when part or all of the inner nucleus pulposus protrudes thru the annulus (see FIG. 1).

The pathophysiology of disc disease is believed to be a combination of mechanical compression of the spinal neve by the disc and the local increase of inflammatory substances around the spinal nerve root.(1,2,3) There is evidence that points to a specific inflammatory molecule, called tumor necrosis factor alpha that is released in damaged, degenerated disc.(1,4)

The most common cause of PDDS is a degenerative process in which, as humans age, the disc becomes less hydrated and weakens. This process will lead to progressive disc degeneration, causing chronic spinal pain which often radiates into the arms and legs.

The second most common cause of PDDS is trauma. In this case, the subject will likely recall an inciting injury, often due to lifting and twisting.

Disc disease is the underlying etiology in less than 5% of the population of subjects with back pain.(5) The incidence of a herniated disc is about 5 to 20 cases per 1000 adults annually, and is most common in 30-50-year-olds, with a male/female ratio of 2:1.(5) Lumbar disc herniation alone affects more than 3 million people in the United States every year.

Between 85-90% of subjects with pain/symptoms associated with disc disease will resolve within 8-12 weeks with or without treatment. There are several conventional treatments available to address pain related to disc injury/disease. The therapies, for example, include massage, physical therapy, acupuncture, and chiropractic, along with medications such as ibuprofen, naproxen, aspirin and acetaminophen.

PDDS is often very painful, and for a subset of subjects, these therapies prove to be ineffective. Unfortunately, there are limited effective conservative treatment modalities for those subjects whose pain is refractory. Currently, the remaining options are continued use of pain medication, interventional procedures, or surgical repair.

Addiction is a serious consequence of ongoing use of pain medications, and there is limited evidence in the use of muscle relaxers such as cyclobenzaprine or oral steroids.(6)

Epidural corticosteroid injections provide a slight questionable short-term improvement but offer no long-term relief.(7) There is limited evidence of the efficacy of epidural injections beyond 3 months, and repeat injections are often utilized.(8,9)

The last option for these treatment resistant subjects is spinal surgery (discectomy or laminectomy) or spinal fusion. The benefits of surgical intervention are moderate and tend to decrease over time following surgery. Some subjects require repeat surgery. Studies have shown that the patients that have had a discectomy, 5-7% require additional discectomy surgery.(10)

Studies have shown that an initial lumbar discectomy is statistically associated with an increased likelihood of a subject requiring lumbar fusion (a more invasive procedure) in the future. The frequency of same level disc herniation requiring additional surgery was about 6% and 22-25% of subjects having had surgery have ongoing chronic pain. Although a severe complication of surgery or interventional procedures are rare, cases of paralysis and death have been reported in the literature.

Subjects suffering from chronic, refractory PDDS need additional treatment options rather than invasive procedures or surgery. Those results are questionable. This invention fulfills this need, as it provides a non-invasive, non-addicting effective pain reducing modality, which addresses the underlying cause of pain, unlike anything currently available.

SUMMARY OF THE INVENTION

In the first aspect of the present disclosure, a pharmaceutical composition comprising of magnesium chloride and colchicine is disclosed. This compound has vasodilating, antispasmodic, anti-inflammatory and antioxidant properties, which are synergistic and result in pain reduction in subjects experiencing chronic, refractory spinal pain with or without radiculopathy. (See FIG. 4 for recommended method).

The composition is in a liquid form which is miscible in 50 cc of saline. In the first aspect, the composition is effective when released directly into a vein of a subject. The compound is administered via an intravenous drip for over 20-30 minutes.

In an embodiment, the composition is infused on 13-15 occasions over a treatment course of 13-15 weeks. In the first aspect, multiple treatment sessions may be provided periodically or at regular intervals.

In a preferred embodiment, the compound containing 1000 mg of magnesium chloride, and 1.0 mg colchicine is administered via an IV "drip" over 20-30 minutes over the course of 13-15 sessions at a frequency rate of 2 times weekly for 3 weeks, followed by 1 time weekly for 4 weeks,
followed by 1 time in two weeks for 1 month,
followed by a treatment one month later.

This is the standard of care for this compound for most subjects in chronic pain due to PDDS.

In alternative embodiments, the dosage range of the compound colchicine content is variable (0.5-1.0 mg) while the dosage of magnesium remains constant. In this aspect, the dosage depends upon subjects age, GFR ranges/CrCL (FIG. 3), response to treatment and the skills of the practitioner. Also consider underlying medical conditions and medications.

In alternative embodiments, the number of treatment sessions and the treatment frequency to achieve effective lasting pain relief is variable, depending upon age of the subject, GFR levels/CrCL and underlying condition, (FIG. 3), treatment response and the judgement of skilled person in the art.

In alternative embodiment, the compound is administered through an IV drip, in one single treatment, with pain medications, to initiate immediate treatment for acute/severe pain with following instructions for continued care.

In yet another aspect, subjects suffering from arthritis in the spine will benefit from the compounds anti-inflammatory properties to provide pain relief.

In yet another aspect, the compound has the ability to reduce broad spectrum inflammation. This is evidenced by the reduction of serum inflammatory markers.

Numerous embodiments of the invention are possible. The previous exemplary embodiments are intended to merely illustrate, and not limit, the breadth and depth of embodiment that can fall within the scope of the appended claims and future claims, which define the invention.

In another embodiment, the composition is administered to the subject through the intravenous drip in multiple sessions to reduce or eliminate pain. In such an embodiment, the number of sessions can be sequentially followed. In alternative embodiments, the number of treatment sessions are based on effective pain relief.

In some embodiments, the dosage range of the composition in each of the treatment sessions is variable.

In alternative embodiments, the dosage range of the composition in each of the treatment sessions remains same.

In the aspect, dosage/amount range of the composition depends upon intensity of inflammatory pain in the subject, age and GFR ranges. (FIG. 3)

In this embodiment of the application the subject should not receive an amount of the compound containing over 1 mg of colchicine at any one treatment session.

In this embodiment of the application the subject should not receive an amount of the compound containing 2 mg of colchicine in any 7-day period.

In another claim, it is noted that there are no specific pharmacological agents developed exclusively for the treatment of chronic, treatment resistant pain due to disc injury or disease.

BRIEF DESCRIPTION OF DRAWINGS

The accompanying FIGS. (FIGS.) illustrate embodiments and serves to explain principles of the disclosed embodiments. It is to be understood, however, that these FIGS. are presented for purposes of illustration only, and not for defining limits of relevant applications.

FIG. 3 shows a graph of normal GFR ranges as it applies to the age of the subject. Also, the stages of kidney disease are outlined along with suggested modifications of dosage per GFR range.

DETAILED DESCRIPTION OF THE INVENTION

Figure 1:
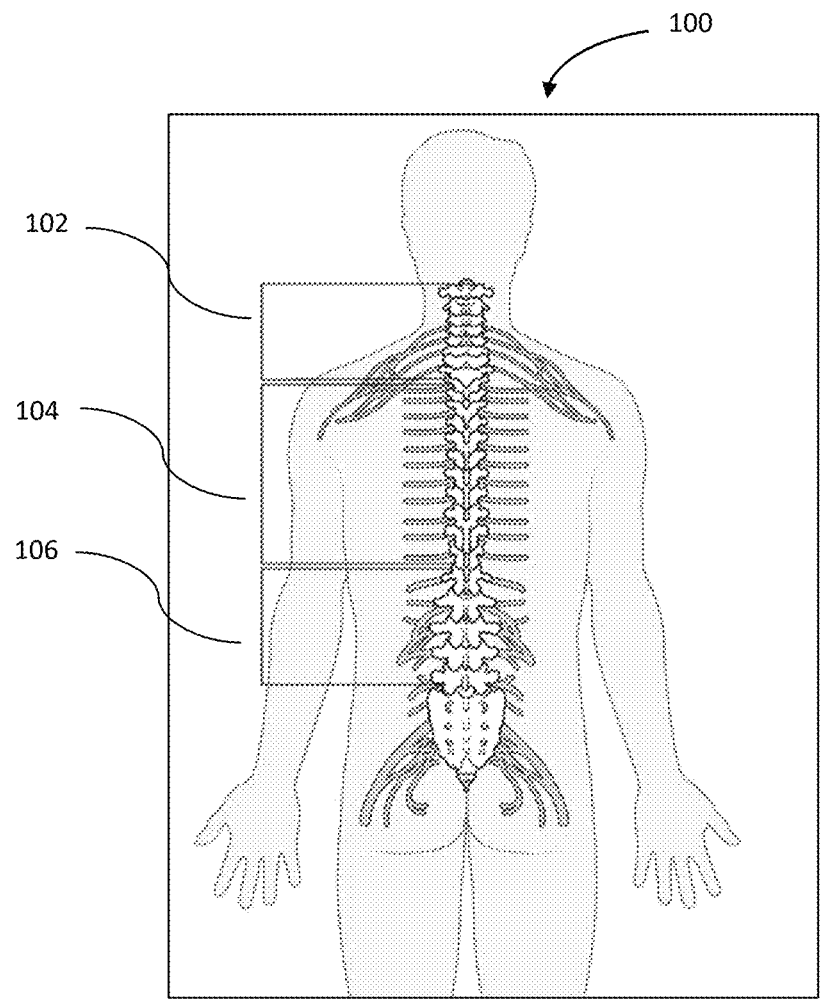
FIG. 1 shows a schematic representation of a living being showing various parts of spine.

For the purpose of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

The term "intravenous" may be referred hereinafter as "IV" and define a route of administration of the disclosed composition. Such a route of administration involves administering the composition directly into a vein. This is done in the form of a "drip" as opposed to an injection. This route of administration of the invention optimizes the synergistic combination of magnesium chloride and colchicine.

The term "radiculopathy" defines a disease of the root of a nerve, such as a pinched nerve which results in symptoms in extremities.

The term "myospasms" defines chronic hypertonic-tight muscles.

The term "vertebral musculature" defines muscles of the spine.

The term "tubulins" refers herein to building blocks of microtubules which are narrow and hollow tubes inside a cell.

The term "mitosis" defines herein a type of cell division that results in two daughter cells each having the same number and kind of chromosomes as the parent nucleus.

The term "half-life" also referred hereinafter as "t ½" defines a period of time required for the concentration or amount of drug in the blood reduced by one-half.

The present application is directed to a pharmaceutical compound containing colchicine and magnesium chloride. This compound has anti-inflammatory, antioxidant, antispasmodic vasodilating properties that result in pain reduction/elimination in subjects experiencing PDDS.

When discs are injured or diseased, they become inflamed, this is the source of much of the pain experienced by subjects experiencing PDDS.

Figure 4:
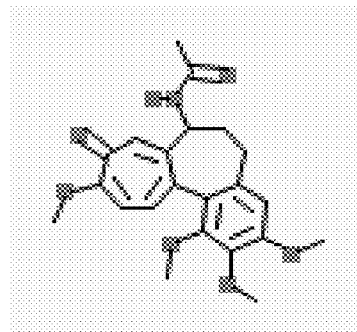
FIG. 4 shows the chemical structure of Colchicine.
Figure 5:
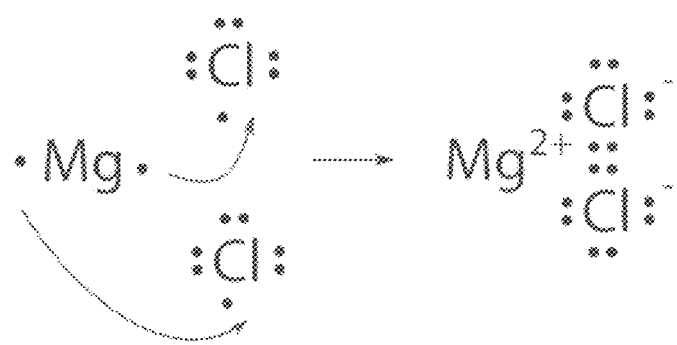
FIG. 5 shows the chemical structure of Magnesium Chloride.

The anti-inflammatory agents in the invention are magnesium chloride and colchicine. (see FIGS. 4 and 5).

Magnesium is known to have anti-inflammatory properties. 50% of the American population is magnesium insufficient and when magnesium is low, increased levels of intracellular calcium ions (Ca++) occur, eliciting calcium activated release of a wide range of pro-inflammatory substances. The addition of magnesium prevents the influx of intracellular ions preventing release of a wide range of pro-inflammatory substances. (11) (see FIG. 5)

Colchicine is known to have anti-inflammatory properties. Colchicine's anti-inflammatory properties reside in its ability to bind to tublin via the tublin-colchicine's binding complex, preventing cell division (mitosis) and the subsequent formation of various pro-inflammatory substances. (12) (see FIG. 4)

Figure 2:
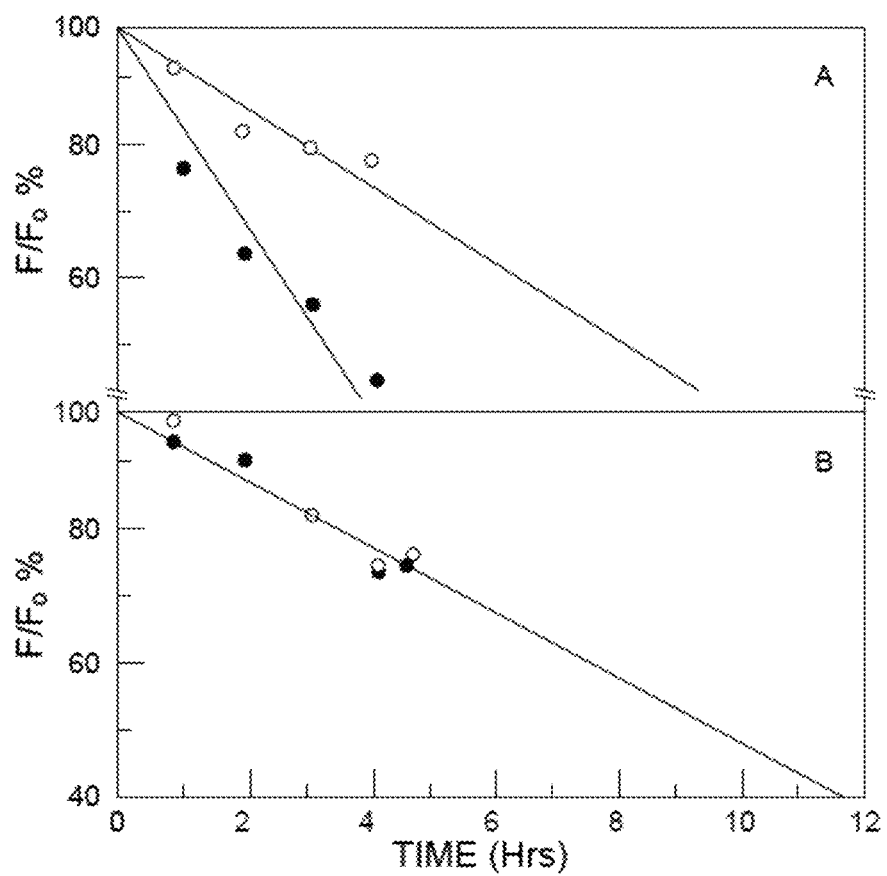
FIG. 2 shows a graph showing loss of AC, a colchicine analog, binding to tubulin as a function of time in the absence and presence of magnesium chloride.

Magnesium, when administered simultaneously with colchicine, enhances colchicine's anti-inflammatory properties. Colchicine anti-inflammatory properties are rooted in its ability to bind to the colchicine-tublin binding complex. (13) The longer the colchicine remains binded, the more pronounced its anti-inflammatory effects. The addition of magnesium to colchicine decreases the off rate of colchicine several fold, increasing the half-life of colchicine from 4-10 hours, thereby enhancing its anti-inflammatory potential. (See FIGS. 2, 4, 5) (13)

The synergistic anti-inflammatory properties of the agents in the invention make it effective for pain relief, unique, and novel.

Magnesium's ability to enhance the tubulin binding capacity of colchicine is a key component of appreciating the effectiveness and uniqueness of the invention.

A component of tissue injury in the body, including intervertebral discs, is that of oxidant pathology or stress. Colchicine has antioxidant properties. (14) Magnesium's role as an antioxidant is well established. (15)

The synergistic anti-oxidative properties of the invention help make this compound effective, unique, and novel.

Intervertebral discs have an inherently poor blood supply, this is well known. Because of this poor blood supply, discs are notorious for slow healing. Magnesium has vasodilating effects due to its influence on smooth muscle, which becomes pronounced and immediate upon IV administration. The vasodilating effect increases circulation throughout the body, including the intervertebral discs. The simultaneous IV administration of magnesium chloride and colchicine allows for easier entry and longer exposure of colchicine to damaged, inflamed areas of the disc (s).

Sources of pain in PDDS reside in inflammation in the disc and spasm of the spinal musculature. The invention has pain relieving properties in the treatment of PDDS. The pain-relieving agents in this invention are magnesium chloride and colchicine.

Colchicine addresses the inflammatory component of the pain, as does magnesium.

Magnesium addresses vertebral myospasms, a component of pain associated with PDDS, by its anti-spasmodic effect on skeletal musculature.

By addressing both inflammation and myospasms in subjects with PDDS, the compound provides effective pain relief without the use of possibly addicting pain medication.

Figure 6:
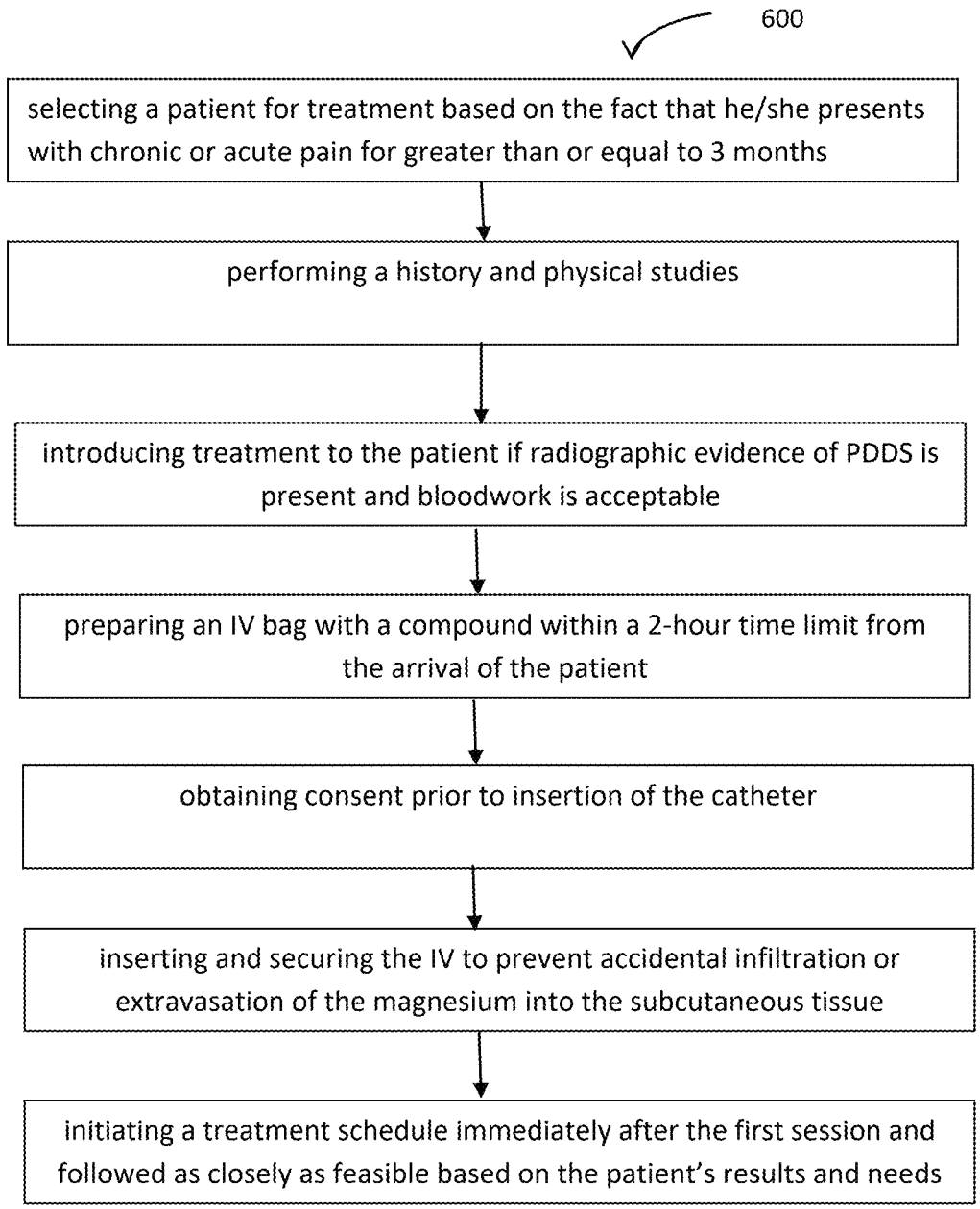
FIG. 6 shows a flowchart depicting a method for providing a treatment to people suffering from PDDS.

In an embodiment, the present disclosure discloses a method 600 for treating a patient suffering from PDDS as shown in FIG. 6. The method involves a number of steps, sequence thereof may be exemplary for the skilled persons to understand the present invention. The method involves selecting a patient for a treatment based on the fact that he/she presents with chronic or acute pain for greater than or equal to 3 months, followed by performing a history and physical studies, including bloodwork and radiographic images. Such studies are performed to include a. Medical history past and present
b. Medications-past and present
c. Bloodwork includes CBC with differential and platelet count, liver function, kidney function and electrolyte balance.

The method further includes introducing treatment to the patient if radiographic evidence of PDDS is present and bloodwork is acceptable. The patient is then introduced to the treatment. Thereafter, an IV bag is prepared with compound within a 2-hour time limit from the arrival of the patient, and a consent is obtained prior to the insertion of the catheter. The patient must be well hydrated before the procedure can take place and dosages may remain constant during each treatment session.

The method further includes inserting and securing the IV to prevent accidental infiltration or extravasation of the magnesium into the subcutaneous tissue. This is to ensure that a chemical burn does not take place. (An IV push through a needle or butterfly type catheter is not recommended as this may cause increased risk of chemical burn.). Then, a treatment schedule is to begin immediately after the first session and followed as closely as feasible based on the patient's results and needs. The treatment is dependent on doctors' assessment of patient's needs.

Numerous embodiments of the invention are possible. The previous exemplary embodiments are intended to merely illustrate, and not limit, the breadth and depth of embodiments that can fall within the scope of the appended claims and future claims, which define the invention.

What is claimed is:

1. A method for providing a treatment to a patient diagnosed with painful damaged disc syndrome (PDDS), the method comprising:
  selecting a patient for treatment based on the fact he/she presents with chronic or acute pain for greater than or equal to 3 months;
  performing a history and physical studies, the history and physical studies comprising bloodwork and radiographic images to include medical history past and present, medications—past and present, and bloodwork including CBC with differential and platelet count, liver function, kidney function and electrolyte balance;
  introducing treatment to the patient if radiographic evidence of PDDS is present and bloodwork is acceptable;
  introducing the treatment to the patient by a plurality of steps further comprising:
  preparing an IV bag with a compound within a 2-hour time limit from the arrival of the patient, the compound comprising at least 1 mg of colchicine as an anti-inflammatory, and 1000 mg of magnesium chloride as an antioxidative, vasodilating, antispasmodic and anti-inflammatory agent;
  obtaining consent prior to insertion of a catheter;
  inserting and securing the catheter to prevent accidental infiltration or extravasation of the magnesium into a subcutaneous tissue; and
  initiating a treatment schedule immediately after the first session and followed as closely as feasible based on the patient's results and needs.

* * * * *